United States Patent
Oura et al.

(10) Patent No.: US 11,464,496 B2
(45) Date of Patent: Oct. 11, 2022

(54) PATIENT MONITOR, VITAL SIGN SOFTWARE CONTROL METHOD, AND PROGRAM

(71) Applicant: NIHON KOHDEN CORPORATION, Tokyo (JP)

(72) Inventors: Mitsuhiro Oura, Tokyo (JP); Sou Kumagai, Tokyo (JP); Wataru Matsuzawa, Tokyo (JP); Nobuyuki Yasumaru, Tokyo (JP); Kazuya Nagase, Tokyo (JP); Hiroshi Torigai, Tokyo (JP); Naoki Fukushima, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 336 days.

(21) Appl. No.: 15/781,954

(22) PCT Filed: Dec. 6, 2016

(86) PCT No.: PCT/JP2016/005069
§ 371 (c)(1),
(2) Date: Jun. 6, 2018

(87) PCT Pub. No.: WO2017/098723
PCT Pub. Date: Jun. 15, 2017

(65) Prior Publication Data
US 2018/0353160 A1    Dec. 13, 2018

(30) Foreign Application Priority Data

Dec. 7, 2015 (JP) .............................. JP2015-238119
Dec. 1, 2016 (JP) .............................. JP2016-234159

(51) Int. Cl.
*A61B 8/00* (2006.01)
*G16H 40/63* (2018.01)
(Continued)

(52) U.S. Cl.
CPC .............. *A61B 8/543* (2013.01); *A61B 5/743* (2013.01); *A61B 8/4416* (2013.01); *A61B 8/463* (2013.01);
(Continued)

(58) Field of Classification Search
CPC .. A61B 8/543; A61B 8/54; A61B 8/56; A61B 5/743; A61B 8/4416; A61B 8/463;
(Continued)

(56) References Cited

U.S. PATENT DOCUMENTS 5,733,247 A * 3/1998 Fallon .................. A61B 5/0017
324/309
6,450,958 B1   9/2002 Linkhart et al.
(Continued)

FOREIGN PATENT DOCUMENTS

CN      101297751 A    11/2008
CN      102857550 A    1/2013
(Continued)

OTHER PUBLICATIONS

International Search Report dated Mar. 1, 2017 issued by the International Searching Authority in counterpart International Patent Application No. PCT/JP2016/005069 (PCT/ISA/210).
(Continued)

Primary Examiner — Joseph M Santos Rodriguez
Assistant Examiner — Kaitlyn E Sebastian
(74) Attorney, Agent, or Firm — Sughrue Mion, PLLC

(57) ABSTRACT

A patient monitor that acquires and displays first vital sign information and second vital sign information of a subject includes an event detection unit that is configured to detect an activation start event for starting an activation process of biological information processing software which performs a process pertaining to the second vital sign information and an activating event for activating the biological information
(Continued)

processing software and a software control unit that causes the biological information processing software to be in a standby state, in which a part of the activation process of the biological information processing software has been performed, when the activation start event is detected by the event detection unit, and causes the biological information processing software to be in an active state from the standby state when the activating event is detected by the event detection unit.

10 Claims, 7 Drawing Sheets

(51) Int. Cl.
| | |
|---|---|
| *A61B 5/00* | (2006.01) |
| *G16H 20/40* | (2018.01) |
| *G16H 30/20* | (2018.01) |
| *A61B 5/024* | (2006.01) |
| *A61B 5/08* | (2006.01) |
| *A61N 1/39* | (2006.01) |
| *A61B 5/021* | (2006.01) |
| *A61B 5/01* | (2006.01) |
| *A61B 5/318* | (2021.01) |

(52) U.S. Cl.
CPC .............. *A61B 8/54* (2013.01); *A61B 8/56* (2013.01); *G16H 20/40* (2018.01); *G16H 30/20* (2018.01); *G16H 40/63* (2018.01); *A61B 5/01* (2013.01); *A61B 5/021* (2013.01); *A61B 5/024* (2013.01); *A61B 5/0816* (2013.01); *A61B 5/318* (2021.01); *A61B 8/467* (2013.01); *A61B 2560/0209* (2013.01); *A61N 1/39* (2013.01)

(58) Field of Classification Search
CPC ....... A61B 5/024; A61B 5/0816; A61B 8/467; A61B 5/021; A61B 2560/0209; A61B 5/0402; A61B 5/01; G16H 20/40; G16H 30/20; G16H 40/63; A61N 1/39
See application file for complete search history.

(56) References Cited

U.S. PATENT DOCUMENTS

| | | | |
|---|---|---|---|
| 2003/0093503 A1* | 5/2003 | Yamaki ................. | G16H 40/63 709/220 |
| 2003/0163045 A1 | 8/2003 | Gatzke | |
| 2004/0249279 A1 | 12/2004 | Maschke | |
| 2007/0016034 A1* | 1/2007 | Donaldson ........... | A61B 8/0833 600/437 |
| 2008/0270037 A1 | 10/2008 | Nakada | |
| 2010/0149085 A1* | 6/2010 | Kim .................... | G09G 3/3426 345/102 |
| 2013/0002431 A1* | 1/2013 | Enomoto ............ | H04L 12/2823 340/573.1 |
| 2014/0125477 A1* | 5/2014 | Kasuya ................. | G16H 40/63 340/525 |
| 2014/0323870 A1 | 10/2014 | Satsuka et al. | |
| 2014/0366878 A1* | 12/2014 | Baron .................. | A61B 5/0036 128/204.23 |
| 2015/0223782 A1* | 8/2015 | Yamagata ........... | A61B 8/5292 600/462 |
| 2016/0183921 A1* | 6/2016 | Li ........................ | A61B 8/5223 600/438 |
| 2016/0220225 A1 | 8/2016 | Wang et al. | |

FOREIGN PATENT DOCUMENTS

| | | |
|---|---|---|
| CN | 104055532 A | 9/2014 |
| CN | 104546010 A | 4/2015 |
| CN | 104703548 A | 6/2015 |
| JP | 7-171115 A | 7/1995 |
| JP | 2014-073273 A | 4/2014 |
| JP | 2014-213028 A | 11/2014 |
| WO | 2009/138902 A1 | 11/2009 |
| WO | 2015/051619 A1 | 4/2015 |

OTHER PUBLICATIONS

Written Opinion dated Mar. 1, 2017 issued by the International Searching Authority in counterpart International Patent Application No. PCT/JP2016/005069 (PCT/ISA/237).
Communication dated Sep. 29, 2020, issued by the Japanese Intellectual Property Office in counterpart Japanese Application No. 2016-234159.
Communication dated Jul. 27, 2020, issued by the State Intellectual Property Office of P.R. China in counterpart Chinese Application No. 201680071851.2.

* cited by examiner

FIG. 7

| USE MODE | ACTIVATION START EVENT | ACTIVATING EVENT |
|---|---|---|
| ICU MODE | MONITOR ACTIVATION | PROBE DETECTION |
| OPERATING ROOM MODE | PROBE DETECTION | RECEIVED SIGNAL CHANGES |
| WARD MODE | VITAL SIGN HAS ABNORMAL VALUE | RECEIVED SIGNAL CHANGES |
| ABDOMINAL DISEASE MODE | ACCELERATION IS EQUAL TO OR MORE THAN PREDETERMINED VALUE | PROBE DETECTION |
| ... | ... | ... |

PATIENT MONITOR, VITAL SIGN SOFTWARE CONTROL METHOD, AND PROGRAM

TECHNICAL FIELD

The present invention relates to a patient monitor, a vital sign software control method, and a program.

BACKGROUND ART

Various vital signs (a blood pressure, a body temperature, breathing, a pulse rate, arterial oxygen saturation and the like) are widely used as information for understanding the state of a subject. Furthermore, an ultrasonic inspection system is used in order to understand the states of a breast, an abdomen and the like of a subject.

In recent years, there has been proposed a technology for simultaneously performing vital signs measurement and ultrasonic diagnosis. For example, a system is disclosed in PTL 1 in which an ultrasonic transducer can be connected to a patient monitor (see FIG. 1 of PTL 1). The system can simultaneously process both ultrasonic images acquired by the ultrasonic transducer and vital parameters (vital signs) of a subject.

CITATION LIST

Patent Literature

[PTL 1]
WO/2009/138902

SUMMARY OF INVENTION

Technical Problem

As one application field of a system capable of simultaneously performing vital signs measurement and ultrasonic diagnosis, there is emergency medical care and an operating room. In a use scene thereof, it is necessary to immediately acquire ultrasonic images and to quickly know a disease state. However, an activation process of ultrasonic software requires complicated setting and processing. Therefore, there is a case that it is not possible to quickly refer to the ultrasonic images and a case that the activation of the ultrasonic software becomes an obstacle of execution of other types of software.

The aforementioned problems are not limited to the emergency medical care and the operating room, and are common in wide scenes in which ultrasonic images should be quickly displayed in a patient monitor that measures vital signs. Furthermore, the problems are common in the case in which a brain wave measuring device and an electric impedance tomography signal measuring device are connected to the patient monitor as well as the case in which ultrasonic diagnostic equipment is connected to the patient monitor.

The present invention is made to solve the above-described problem, and an object of the present invention is to provide a patient monitor that reduces an activation load of biological information processing software related to another type of vital sign (second vital sign information, for example, ultrasonic image) when vital sign (the first vital sign information) and the second vital sign information are displayed, a vital sign software control method, and a program.

Solution to Problem

According to an aspect of the present invention, a patient monitor that acquires and displays first vital sign information and second vital sign information of a subject, includes an event detection unit that is configured to detect an activation start event for starting an activation process of biological information processing software which performs a process pertaining to the second vital sign information and an activating event for activating the biological information processing software, and a software control unit that causes the biological information processing software to be in a standby state, in which a part of the activation process of the biological information processing software has ended, when the activation start event is detected by the event detection unit, and causes the biological information processing software to be in an active state from the standby state when the activating event is detected by the event detection unit.

The software control unit set the biological information processing software in the standby state in advance, and then cause the biological information processing software to be in the active state. That is, the biological information processing software is activated with two steps. The biological information processing software is activated halfway in advance, and the biological information processing software can be completely activated with small processing from the standby state.

Advantageous Effects of Invention

According to an aspect of the patient monitor according to the present invention, when the first vital sign information (vital sign) and the second vital sign information (for example, ultrasonic image) of a subject are acquired and displayed, it is possible to reduce a load of the activation process of the biological information processing software for the second vital sign information.

BRIEF DESCRIPTION OF DRAWINGS

FIG. 7 is a conceptual diagram illustrating an operation of an event detection part 181 according to a fourth embodiment.

DESCRIPTION OF EMBODIMENTS

First Embodiment

Figure 1:
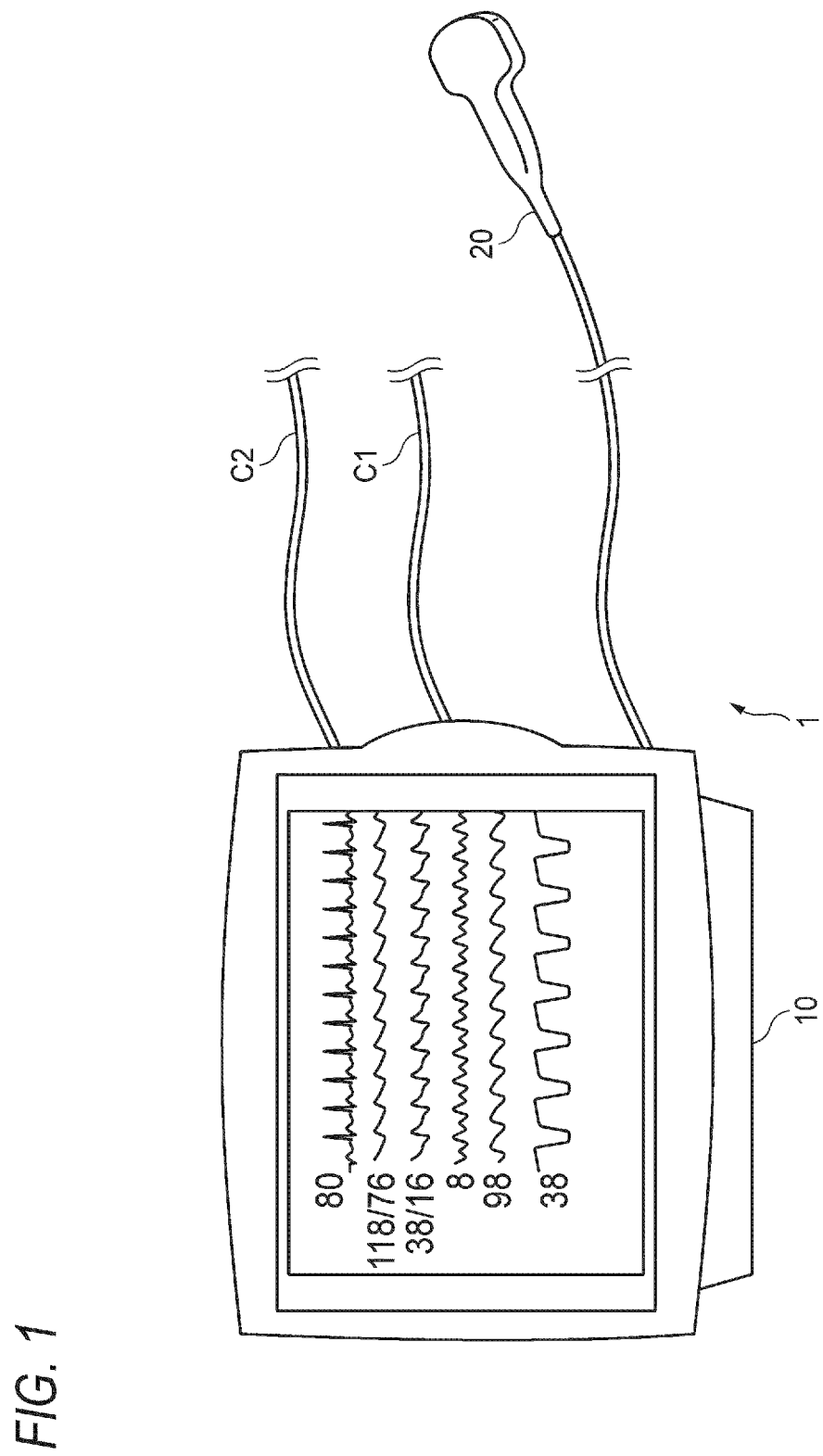
FIG. 1 is a diagram illustrating an external appearance configuration example of a vital sign measuring system 1 according to a first embodiment.

Hereinafter, embodiments of the present invention will be described with reference to each of drawings. FIG. 1 is a conceptual diagram illustrating an external appearance configuration of a vital sign measuring system 1 according to the present embodiment. The vital sign measuring system 1 has a patient monitor 10 and an ultrasonic measuring device 20. Although not illustrated, the patient monitor 10 is appropriately connected to sensors 30 (which will be described later) via cable lines C1 and C2.

The ultrasonic measuring device 20 is connected to the patient monitor 10 via a cable. The ultrasonic measuring device 20 is an example of a device that acquires vital sign (second vital sign information) of a subject, and is a device for acquiring ultrasonic image of a subject's internal body in the present example. The patient monitor 10 acquires the ultrasonic image (the second vital sign) from the ultrasonic measuring device 20, and acquires various vital signs (first vital sign information) via the sensors 30.

The patient monitor 10 measures various vital signs (the first vital sign information) based on biological signals acquired from the sensors 30 (which will be described later in FIG. 2) connected to the subject. The sensors 30 connected to the subject are various sensors which are used for measuring the vital signs. For example, the sensor 30 includes a cuff used for measuring a blood pressure, an electrode used for measuring an electrocardiogram and the like (a disposable electrode, a clip electrode and the like), a SpO2 probe, a mask for measuring breathing, and the like. In addition, the sensor 30 may acquire biological signals by an invasive method. Furthermore, vital signs to be measured, for example, are a blood pressure, a body temperature, a breathing rate, pulse rate, arterial oxygen saturation, an electrocardiogram, a pulse rate and the like. The patient monitor 10 includes, for example, a bedside monitor, a transport monitor, a portable medical telemeter, and a defibrillator having a function of measuring an electrocardiogram. The bedside monitor may be used in a treatment room and an operating room of emergency medical care, or may be used in a general ward and the like. That is, the patient monitor 10 should be interpreted as various medical devices that measure and display vital signs. In the following description, the patient monitor 10 is assumed as a so-called bedside monitor.

The patient monitor 10 has connection ports (for example, insertion ports of connectors) for being connected to the sensors 30. The ultrasonic measuring device 20 is a device detachable from the connection ports. The ultrasonic measuring device 20 causes a probe 21 (which will be described later) to make contact with a subject's body, thereby acquiring ultrasonic images of a subject's internal body. The ultrasonic measuring device 20 is a device having a weight and a size which can be grasped by a user (mainly, a doctor), and has a shape in which a cable has been connected to a probe head of a general ultrasonic diagnostic equipment.

The ultrasonic measuring device 20 is not limited to the wired connection as illustrated in the drawing, and may transmit/receive data to/from the patient monitor 10 by a wireless connection.

Figure 2:
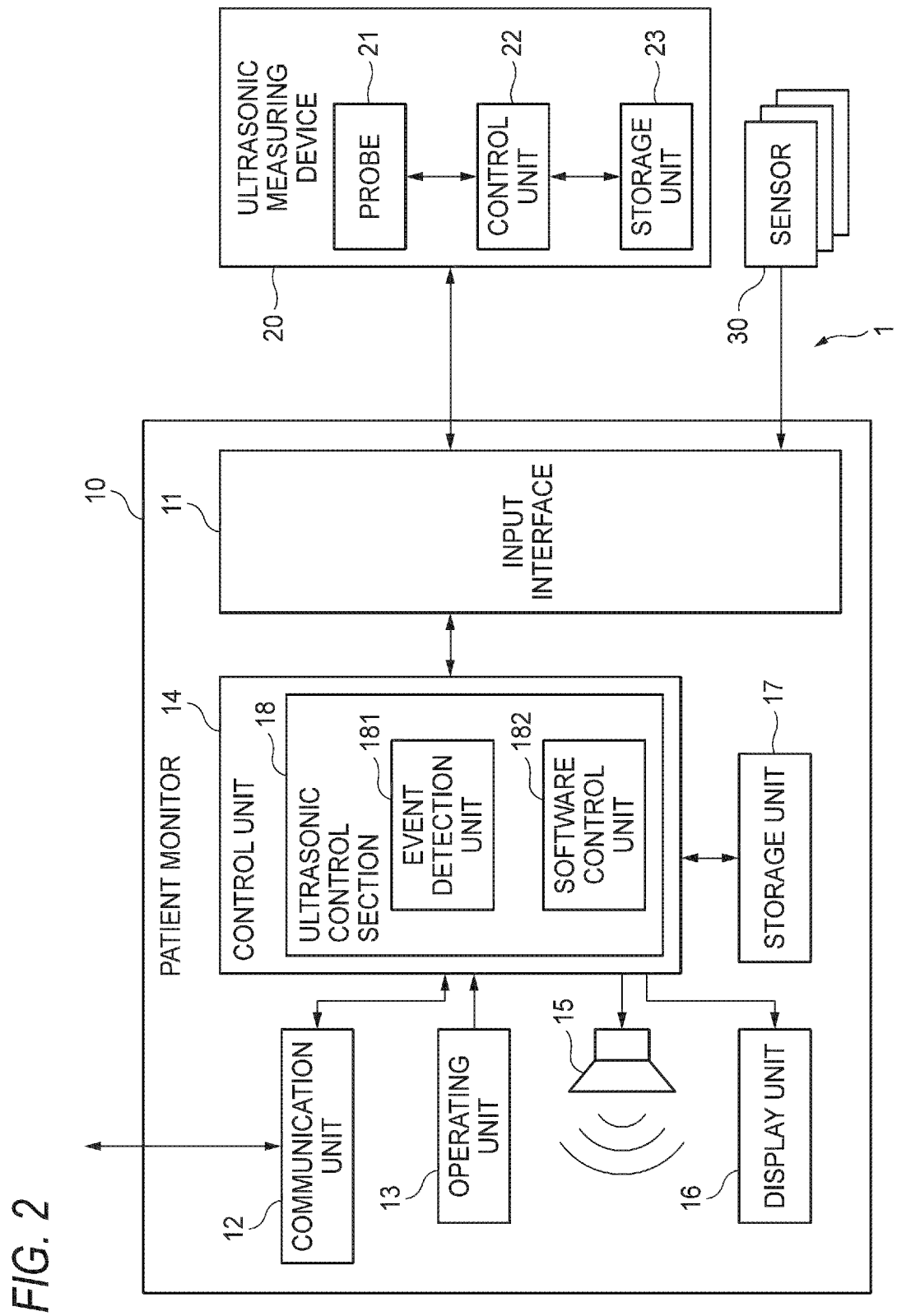
FIG. 2 is a block diagram illustrating an internal configuration of the vital sign measuring system 1 according to the first embodiment.

Subsequently, with reference to FIG. 2, an electrical configuration of the vital sign measuring system 1 will be described. FIG. 2 is a block diagram focused on the electrical configuration of the vital sign measuring system 1.

First, the ultrasonic measuring device 20 will be described. The ultrasonic measuring device 20 is a device detachable from the patient monitor 10 as illustrated in FIG. 1. The ultrasonic measuring device 20 has a so-called shape similar to a probe. The ultrasonic measuring device 20 has the probe 21, a control unit 22, and a storage unit 23. The ultrasonic measuring device 20 may be a device that operates by receiving power from the patient monitor 10, or may be configured to have an internal power source.

The probe 21 makes contact with (or makes close to) a subject's body and irradiates ultrasonic waves. The probe 21 receives reflected ultrasonic waves (reflected waves). The probe 21 supplies the received ultrasonic waves to the control unit 22.

The control unit 22 performs reception and the like of various types of setting of the probe 21 and received signals acquired by the probe 21. For example, processes of the control unit 22 are as follows.

Setting of an ultrasonic frequency of the probe 21
Beam-forming setting of the probe 21
Arithmetic processing (matching addition of reflection echo signal) of reflected waves received in the probe 21 and formation of ultrasonic reception beam
Mode signal processing, CF signal processing, and Doppler signal processing for ultrasonic reception beam
Formation of ultrasonic image by scan processing
Switching process of an ultrasonic mode (B mode, M mode, D mode and the like)
Error detection of the probe 21
Data transmission/reception with the patient monitor 10 (also including ultrasonic image).

The control unit 22 transmits the ultrasonic images generated by the aforementioned processes to the patient monitor 10. The control unit 22 may transmit signals of the reflected waves acquired by the probe 21 to the patient monitor 10 as is. In this case, a control unit 14 performs a process of generating ultrasonic images based on the signals of the reflected waves.

The storage unit 23 stores various programs (including system software and various types of application software) used by the control unit 22, and data (including a history value, a setting value and the like of ultrasonic image). The control unit 22 appropriately reads the programs and the data from the storage unit 23. The control unit 22 appropriately writes data in the storage unit 23. The storage unit 23 is a secondary storage device provided in the ultrasonic measuring device 20, and for example, is a hard disk provided in the ultrasonic measuring device 20.

The ultrasonic measurement device 20 may generate the ultrasonic image from the reflected waves and transmit the generated ultrasonic image to the patient monitor 10. Also, the ultrasonic measurement device 20 may simply generate a signal indicating the reflected waves to the patient monitor.

Subsequently, the sensor 30 and the patient monitor 10 will be described. The sensor 30 is a sensor for vital signs, which is connected to a subject's body as described above.

The patient monitor 10 has an input interface 11, a communication unit 12, an operating unit 13, the control unit 14, a speaker 15, a display unit 16, and a storage unit 17. Although not clearly indicated, the patient monitor 10 also appropriately includes an internal power source.

The input interface 11 includes the aforementioned connection ports, peripheral circuits thereof, and the like. The input interface 11 supplies the control unit 14 with data received from the sensor 30 and the ultrasonic measuring device 20. Furthermore, the input interface 11 transmits data to the sensor 30 or the ultrasonic measuring device 20 from the patient monitor 10. The patient monitor 10 receives ultrasonic images (or received signals serving as a basis of the ultrasonic images) from the ultrasonic measuring device 20.

The communication unit 12 transmits/receives data to/from another device (for example, a central monitor). For example the communication unit 12 may satisfy a communication standard according to a wireless LAN (Local Area Network) and the like. The communication unit 12 may perform a communication process by using a wired cable.

A user (mainly, a doctor) inputs data to the patient monitor 10 via the operating unit 13. The operating unit 13, for example, includes a button, a knob, a rotary selector, a key and the like provided on a casing of the patient monitor 10. The data input via the operating unit 13 is supplied to the control unit 14.

The speaker 15 outputs various types of notification sound including an alarm. The speaker 15 performs notification under the control of the control unit 14.

The display unit 16 includes a display, a peripheral circuit thereof, and the like provided on the casing of the patient monitor 10. The display unit 16 displays various types of information of a subject. More specifically, the display unit 16 displays information (waveforms and measured values) on various vital signs, a setting screen and the like under the control of the control unit 14. The display unit 16 also displays ultrasonic images under the control of the control unit 14.

The operating unit 13 and the display unit 16 may be configured to be integrally formed with each other (a so-called touch panel-like configuration).

The storage unit 17 stores various programs (including system software and various types of application software) used in the control unit 14 and data (including a blood pressure, a measured value and a setting value of SpO2 and the like, ultrasonic images to be described later and the like). The control unit 14 appropriately reads the programs and the data from the storage unit 17. Furthermore, the control unit 14 appropriately writes data in the storage unit 17. The storage unit 17 is a secondary storage device provided in the patient monitor 10, and for example, is a hard disk provided in the patient monitor 10. The storage unit 17 is not limited to the case of being embedded in the patient monitor 10, and may be configured to be detachable from the patient monitor 10 (for example, a USB (Universal Serial Bus) memory and the like detachable from the patient monitor 10).

The control unit 14 performs various processes of the patient monitor 10. The control unit 14 is configured with a CPU (Central Processing Unit) and a peripheral circuit thereof, and performs its operations by software or hardware. More specifically, the control unit 14 performs acquirement of information (waveforms and measured values of a blood pressure, SpO2, a body temperature and the like) of vital signs based on the biological signals acquired from the sensors 30, ringing control of an alarm based on the information of the vital signs.

The control unit 14 includes an ultrasonic control section 18 that activates/executes ultrasonic software (biological information processing software) for displaying the ultrasonic images (the second vital sign information) from the ultrasonic measuring device 20. In detail, the ultrasonic software performs some kinds of processes related to displaying the ultrasonic image, the processes including obtaining the ultrasonic image from the ultrasonic measuring device 20, writing/reading data into/from the storage unit 17, adjusting image quality, drawing process, and the like. The ultrasonic software may have a configuration which is capable of some kinds of processes related to the ultrasonic image (transmitting data to an external device and the like), which is not limited to the display process. Namely, the ultrasonic software (the biological information processing software) is a software performing some kind of processes related to the ultrasonic image (the second vital sing information). The ultrasonic control section 18 includes an event detection part 181 and a software control part 182.

The event detection part 181 detects an activation start event for starting the activation of the ultrasonic software. The event detection part 181 detects an activating event for changing a state of the ultrasonic software into active. The event detection part 181 detects the occurrence of the activation start event and the activating event as a so-called resident process.

The software control part 182 performs at least a part of the activation process of the ultrasonic software when the activation start event is detected. The activation process, for example, includes the following processes.

Reading of setting data and an ending state

Ensuring of a work memory area

Reading of a register and writing to the register

Establishment (for example, performance of processes decided in USB standard and processes related to a wireless communication standard) of connection with the ultrasonic measuring device 20

Drawing process of software (an application) to a display

For example, when the activation start event is detected, the software control part 182 performs an activation process other than drawing. A state, in which a part of the activation process has ended as described above, is called a standby state. That is, when the activation start event has occurred, the software control part 182 performs a part of the activation process of the ultrasonic software and causes the ultrasonic software to proceed to the standby state.

When the activating event has occurred, the software control part 182 performs all activation processes. A state, in which all the activation processes have ended, is called an active state. That is, when the activating event has occurred, the software control part 182 causes the ultrasonic software to proceed to the active state from the standby state.

An example of the activation start event detected by the event detection part 181 will be described below. A user can arbitrarily set the activation start event by operating the operating unit 13. The example of the activation start event, for example, includes the following.

Power ON of the patient monitor 10

Physical connection (insertion and the like of a probe to a USB connection port) of the ultrasonic measuring device 20

When at least one of detected values of various sensors (not illustrated, for example, an acceleration sensor, an impact sensor, an attitude sensor, a pressure sensor, a temperature sensor and the like attached to the sensors 30) are equal to or more than a predetermined value When a received signal from the ultrasonic measuring device 20 has changed When at least one of vital signs (a blood pressure, a body temperature, a breathing rate and the like) has been an abnormal value When at least one of vital signs (a blood pressure, a body temperature, a breathing rate and the like) has been changed from an abnormal value to a normal value When a vital sign is being measured and a battery level is equal to or more than 80%

When time set in advance by a user has reached (for example, 14:00, 16:00, or 18:00)

When an interval set in advance by a user has passed (for example, when three hours have passed from previous ultrasonic diagnosis)

When the patient monitor 10 itself proceeds to a normal operation mode from a power saving mode When sound of "ultrasonic waves" is detected from an embedded sound collecting device (not illustrated, a microphone and the like) (in this case, the patient monitor 10 has a sound analysis function)

Next, an example of the activating event detected by the event detection part 181 will be described. A user can arbitrarily set the activating event by operating the operating unit 13. The example of the activating event, for example, includes the following.

Physical connection (insertion and the like of a probe to a USB connection port) of the ultrasonic measuring device 20

When a detected value of a sensor (not illustrated, for example, an acceleration sensor, an impact sensor, an attitude sensor, a pressure sensor, a temperature sensor or the like attached to the sensors 30) is equal to or more than a predetermined value When a received signal from the ultrasonic measuring device 20 has changed When at least one of vital signs (a blood pressure, a body temperature, a breathing rate and the like) has been an abnormal value When a mode change (an operating room mode, an ICU mode, a round mode and the like) has occurred The setting of these events may be performed according to use cases. For example, when the patient monitor 10 is used in an operating room, it is desired to be able to immediately activate the ultrasonic software and check the body state of a subject. In this case, for example, "Power ON of the patient monitor 10" may be set as the activation start event and "Physical connection of the ultrasonic measuring device 20" may be set as the activating event. In this way, a doctor and the like can immediately activate the ultrasonic software and quickly check the body state of a subject by using ultrasonic images.

Furthermore, there is considered the case in which "When vital signs are being measured and a battery level is equal to or more than 80%" is set as the activation start event and "Physical connection of the ultrasonic measuring device 20" is set as the activating event. In the case of a transport monitor, it is necessary to avoid that the battery level is 0 during the measurement of the vital signs. According to the aforementioned setting, it is possible to immediately activate the ultrasonic software and reduce consumption of a battery.

Furthermore, when detected values of various sensors have been equal to or more than a predetermined value or when the vital signs have been an abnormal value, it is assumed that there is a change in the condition of a subject. These changes are set as the activation start event or the activating event, so that it is possible to immediately understand the condition of a subject from ultrasonic images.

Furthermore, when a received signal from the ultrasonic measuring device 20 has changed, it is assumed that useful information is received from the ultrasonic measuring device 20. This state is set as the activation start event or the activating event, so that the software control part 182 can immediately activate the ultrasonic software in a necessary scene.

That is, a user may set the activation start event and the activating event in consideration of a use, a subject, a use place and the like.

In addition, the event detection part 181 may further detect an inactivating event. The inactivating event is an event serving as a trigger for changing a state of the ultrasonic software into the standby state or the ending state from the active state. When the inactivating event is occurred, the software control part 182 may allow the ultrasonic software to proceed to the standby state or the ending state from the active state.

An example of the inactivating event will be described below. A user can arbitrarily set the inactivating event by operating the operating unit 13. The example of the inactivating event, for example, includes the following.

Physical removal of the ultrasonic measuring device 20 (removal of a probe from a USB connection port)

Pressing down of a standby button

When at least one of vital signs (a blood pressure, a body temperature, a breathing rate and the like) has been a normal value When a signal from ultrasonic measuring device 20 is not changed for a predetermined time or more When a processing load of the control unit 14 is equal to or more than a predetermined value (for example, when CPU availability is equal to or more than a predetermined value)

When a received signal from the sensor 30 or various sensors (an acceleration sensor and the like), which are not illustrated, has not changed for a predetermined time or more When the patient monitor 10 itself proceeds to a power saving mode In addition, a user can arbitrarily set times for waiting for a signal change from the ultrasonic measuring device 20, the sensors 30, and various sensors (an acceleration sensor and the like). The inactivating event as described above is set, so that it is possible to improve performance of other processes of the patient monitor 10 and to reduce battery consumption.

Figure 3:
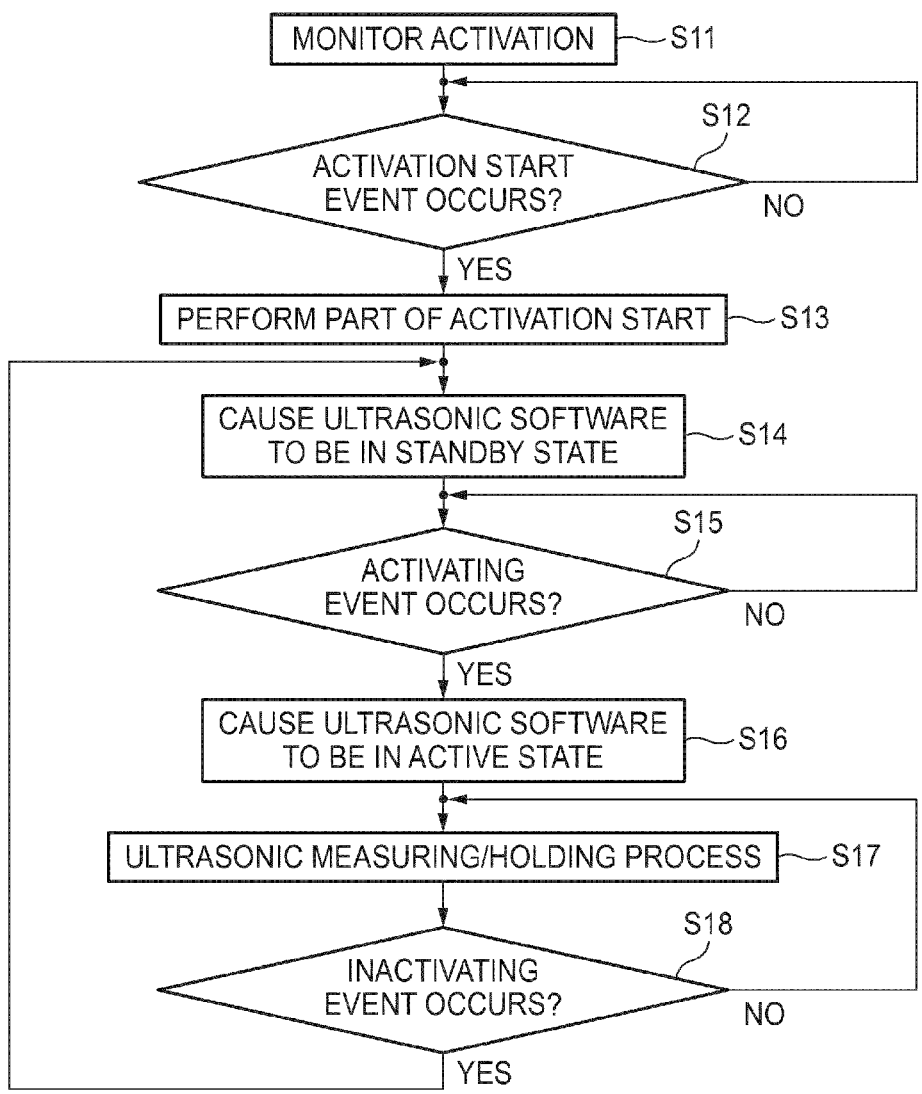
FIG. 3 is a flowchart illustrating an operation of an ultrasonic control section 18 according to the first embodiment.

Subsequently, the flow of processing of the ultrasonic control section 18 (the event detection part 181 and the software control part 182) will be described again with reference to FIG. 3. FIG. 3 is a flowchart illustrating the operation of the ultrasonic control section 18.

The patient monitor 10 starts the activation of the monitor itself by pressing-down of a power ON button, and the like (S11). The event detection part 181 determines whether the activation start event set in advance occurs (S12) after the activation of the monitor (S11). When the activation of the monitor is set as the activation start event, the event detection part 181 determines that the activation start event has occurred at the time of the activation of the monitor.

The event detection part 181 continues monitoring until the activation start event occurs (S12: No). When the activation start event has occurred (S12: Yes), the software control part 182 performs a part of the activation process of the ultrasonic software (S13) and causes the ultrasonic software to be in the standby state (S14).

After the ultrasonic software enters into the standby state, the event detection part 181 monitors whether the inactivating event set in advance occurs (S15). The event detection part 181 continues monitoring until an activating event occurs (S15: No). When the activating event has occurred (S15: Yes), the software control part 182 performs the remaining activation process and causes the ultrasonic software to be in the active state. In this way, a user (mainly, a doctor or a nurse) can refer to the ultrasonic software from a screen.

The user performs a screen operation of the ultrasonic software and an operation of the ultrasonic measuring device 20, diagnoses a subject's internal body by ultrasonic waves, and holds ultrasonic images in the storage unit 17 (S17). Also, the event detection part 181 monitors whether the set inactivating event has occurred (S18).

When the inactivating event has not occurred (S18: No), the event detection part 181 continues monitoring of the inactivating event while continuing the ultrasonic measurement (S17). When the inactivating event has occurred (S18: Yes), the software control part 182 causes the ultrasonic software to proceed to the standby state (S14) from the active state. Although not illustrated, when the inactivating event has occurred, the software control part 182 may end the ultrasonic software itself.

Figure 4:
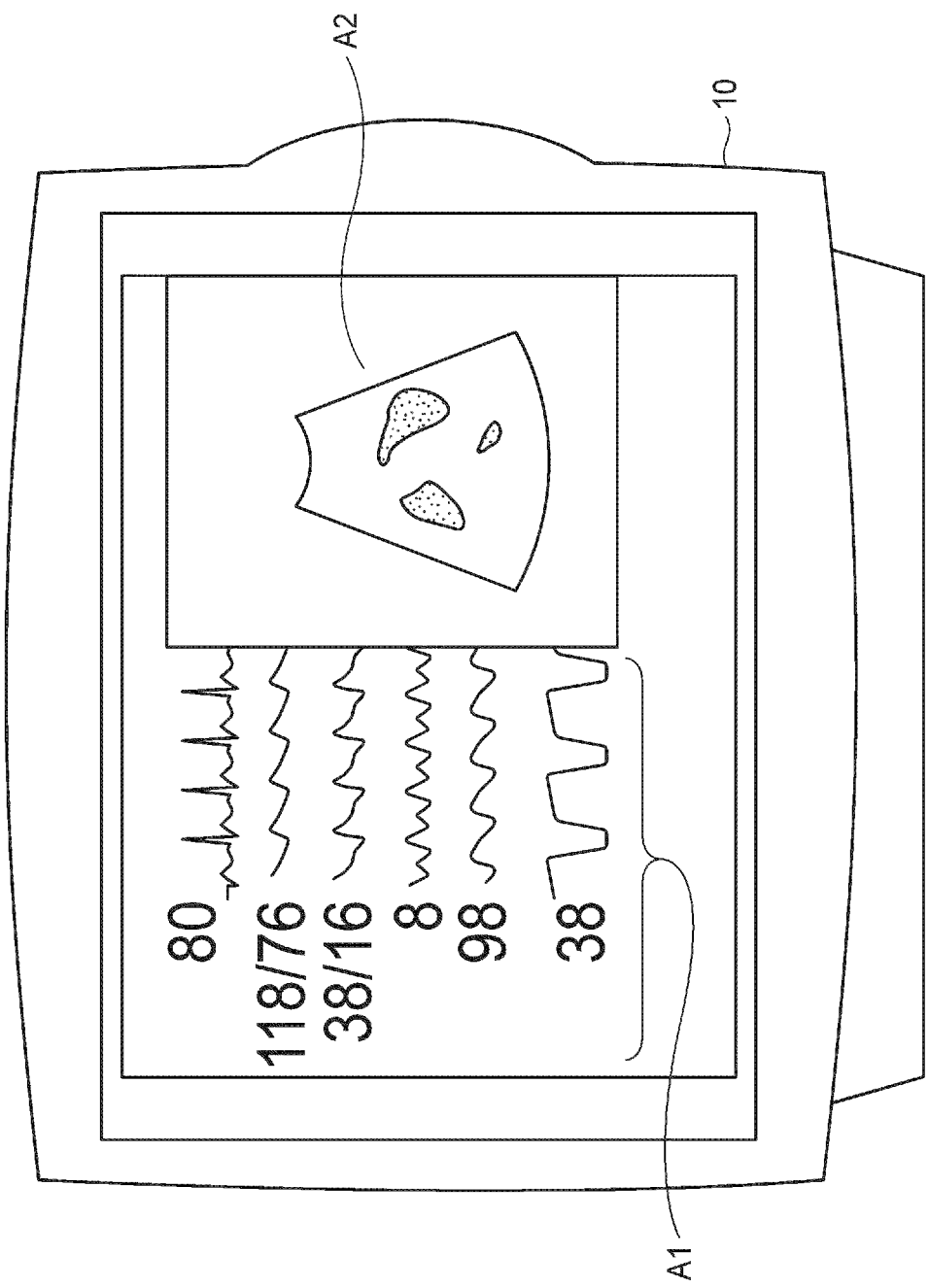
FIG. 4 is a diagram illustrating an example of a display screen of a patient monitor 10 according to the first embodiment.

Next, an example of a display screen when the ultrasonic software has entered into the active state will be described with reference to FIG. 4. As illustrated in the drawing, on the display screen, a display area A1 of vital signs (a blood pressure, a body temperature, a breathing rate and the like), and a display area A2 of ultrasonic images are all displayed. The display area A2 of the ultrasonic images is displayed by a drawing process of the ultrasonic software.

The patient monitor 10 may have a so-called multi-display configuration. In this case, the aforementioned display area A1 (the display area of the vital signs) may be displayed on a first display and the aforementioned display area A2 (the display area of the ultrasonic images) may be displayed on a second display. When the patient monitor 10 has a so-called dual operating system configuration (a configuration in which two or more operating systems internally operate), the drawing processes of the display areas A1 and A2 may be performed by separate operating systems.

Subsequently, the operation and effect of the patient monitor 10 according to the present embodiment will be described. The event detection part 181 detects the activation start event for starting the activation of the ultrasonic software (one type of biological information processing software of the second vital sign information) and the activating event for allowing the ultrasonic software to be active. The software control part 182 causes the ultrasonic software to be in the standby state when the activation start event is detected, and causes the ultrasonic software to proceed to the active state from the standby state when the activating event has occurred. That is, the software control part 182 causes the ultrasonic software to be in the standby state in advance and then causes the ultrasonic software to proceed to the active state (activates the ultrasonic software in two stages). By activating the ultrasonic software halfway in advance, the software control part 182 can immediately allow the ultrasonic software to be in the active state at a low processing load. In this way, a user can immediately use the ultrasonic software even in an emergency scene and the like.

Furthermore, the event detection part 181 detects the inactivating event associated with the inactivation or end of the ultrasonic software. For example, the inactivating event includes removal of the ultrasonic measuring device 20. When the inactivating event is detected, the software control part 182 causes the ultrasonic software to proceed to the standby state (or the ending state). By this control, it is possible to stop a part (or the whole) of processing of the ultrasonic software when it is assumed that no ultrasonic measurement is performed. The part (or the whole) of the processing is stopped, so that it is possible to stabilize measurement of vital signs and reduce battery consumption.

Second Embodiment

Then, the patient monitor 10 according to a second embodiment will be described. The patient monitor 10 according to the present embodiment performs the activation process of the ultrasonic software in consideration of the states of the vital sign as well as the presence or absence of occurrence of the activation start event. The difference between the patient monitor 10 according to the present embodiment and the first embodiment will be described below. In the following description, configurations having the same reference numerals and the same names perform processes similar to those of the first embodiment unless specifically stated otherwise (the same in the following embodiments).

Configurations of the vital sign measuring system 1 and the patient monitor 10 are similar to those of FIGS. 1 and 2. Operations of the ultrasonic control section 18 (the event detection part 181 and the software control part 182) according to the present embodiment will be described with reference to the flowchart of FIG. 5.

In addition to whether the activation start event has occurred after the monitor activation (S11), the event detection part 181 monitors whether the vital sign acquired via the sensor 30 have normal values (S22). The event detection part 181, for example, may determine normality of the vital sign in cooperation with a general alarm detection function. When the vital sign has the normal value together with the occurrence of the activation start event (S22: Yes), the software control part 182 performs a part of the activation process (S13) and causes the ultrasonic software to be in the standby state (S14). That is, even when the activation start event has occurred, if the vital sign has abnormal value, the software control part 182 does not perform the activation process.

Similarly, in addition to whether the activating event has occurred after the proceeding to the standby state (S14), the event detection part 181 monitors whether the vital sign acquired via the sensor 30 have normal value (S25). When the vital sign has the normal value together with the occurrence of the activating event (S25: Yes), the software control part 182 performs all the activation processes and causes the ultrasonic software to be in the active state (S16). That is, even when the activating event has occurred, if the vital sign have abnormal value, the software control part 182 does not complete the activation process. The following processes are similar to those of the first embodiment.

Subsequently, the effect of the patient monitor 10 according to the present embodiment will be described. As described above, when the activation start event has occurred and the vital sign has the normal value, the software control part 182 performs a part of the activation process. When the vital sign has the abnormal value, it is desired to be able to continuously refer to vital sign (a blood pressure, a breathing rate, or electrocardiogram) of a subject. As described above, when the vital sign have the abnormal value, processes related to the ultrasonic software are not performed, so that the patient monitor 10 can stably and continuously acquire the vital sign.

Similarly, when the activating event has occurred and the vital sign has the normal value, the software control part 182 completes the activation process. That is, when the vital sign has the abnormal value, processes related to the ultrasonic software are not performed, so that the patient monitor 10 can stably and continuously acquire the vital sign.

Figure 5:
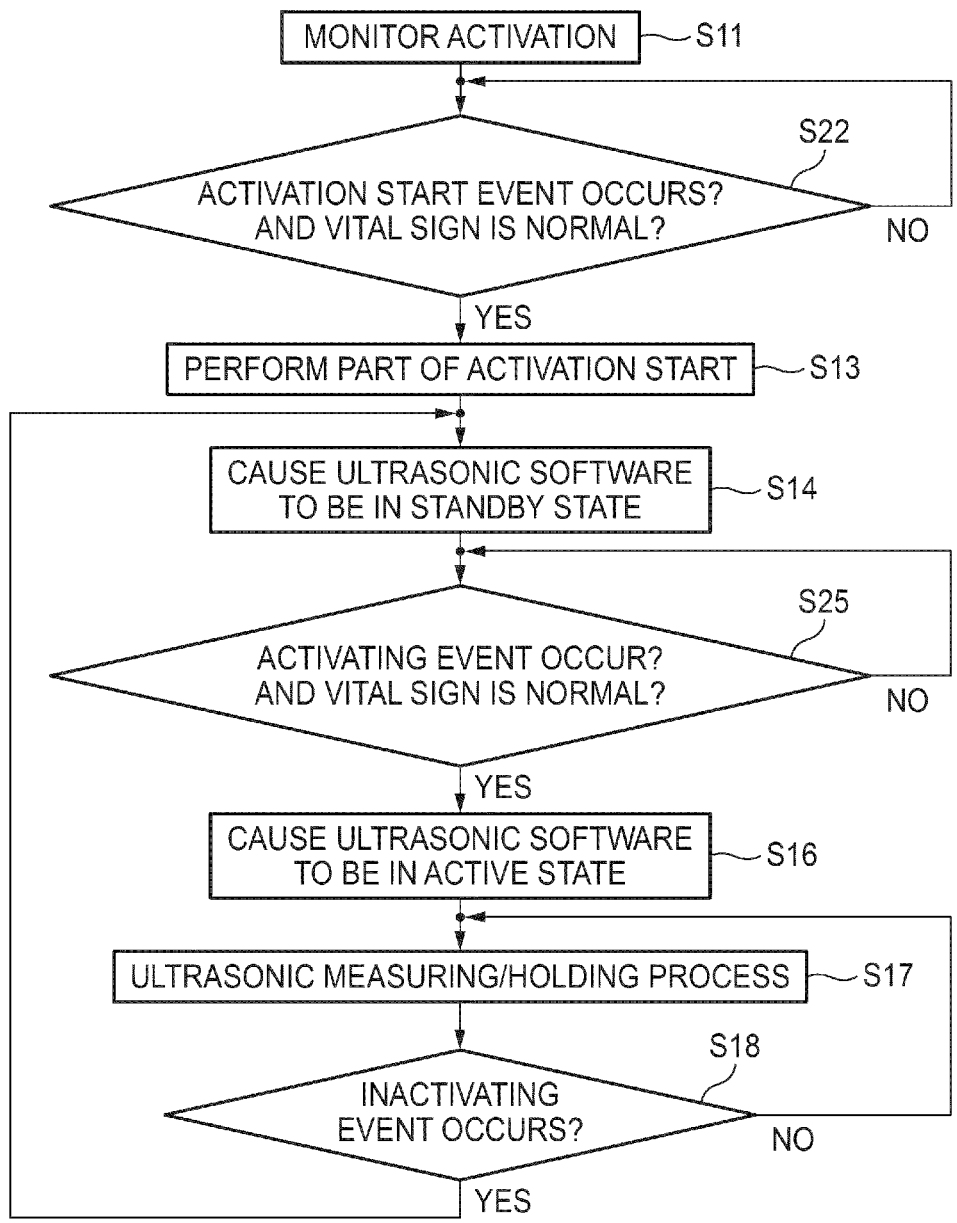
FIG. 5 is a flowchart illustrating an operation of an ultrasonic control section 18 according to a second embodiment.

In addition, the patient monitor 10 can also have a dual operating system configuration as disclosed in JP-2014-23570. With the configuration, a first operating system can measure the vital sign and a second operating system can perform processes related to ultrasonic waves. In the configuration, it is less probable that the ultrasonic processes have an adverse effect on the measurement of the vital sign. Therefore, in the configuration, a user may perform switching setting from the algorithm as illustrated in FIG. 5 to the algorithm illustrated in FIG. 3.

Furthermore, in the case of using the patient monitor 10 with respect to a subject frequently requiring ultrasonic diagnosis (for example, a subject having an abdominal disease), it is assumed to require "it is necessary to perform the ultrasonic diagnosis even when the vital sign has the abnormal value". Therefore, it is desired that a user can explicitly set whether to use the algorithm of FIG. 5.

In consideration of the above, preferably, the patient monitor 10 is configured to receive, from a user, setting regarding whether to consider the normality (abnormality) of the vital sign when the ultrasonic software is activated. The user sets whether to activate the ultrasonic software by using a certain algorithm from the operating unit 13. The ultrasonic control section 18 may activate the ultrasonic software based on the setting.

Third Embodiment

In the patient monitor 10 according to the present embodiment, a user can explicitly designate activation completion of the ultrasonic software. The difference between the patient monitor 10 according to the present embodiment and the first embodiment will be described below.

Figure 6:
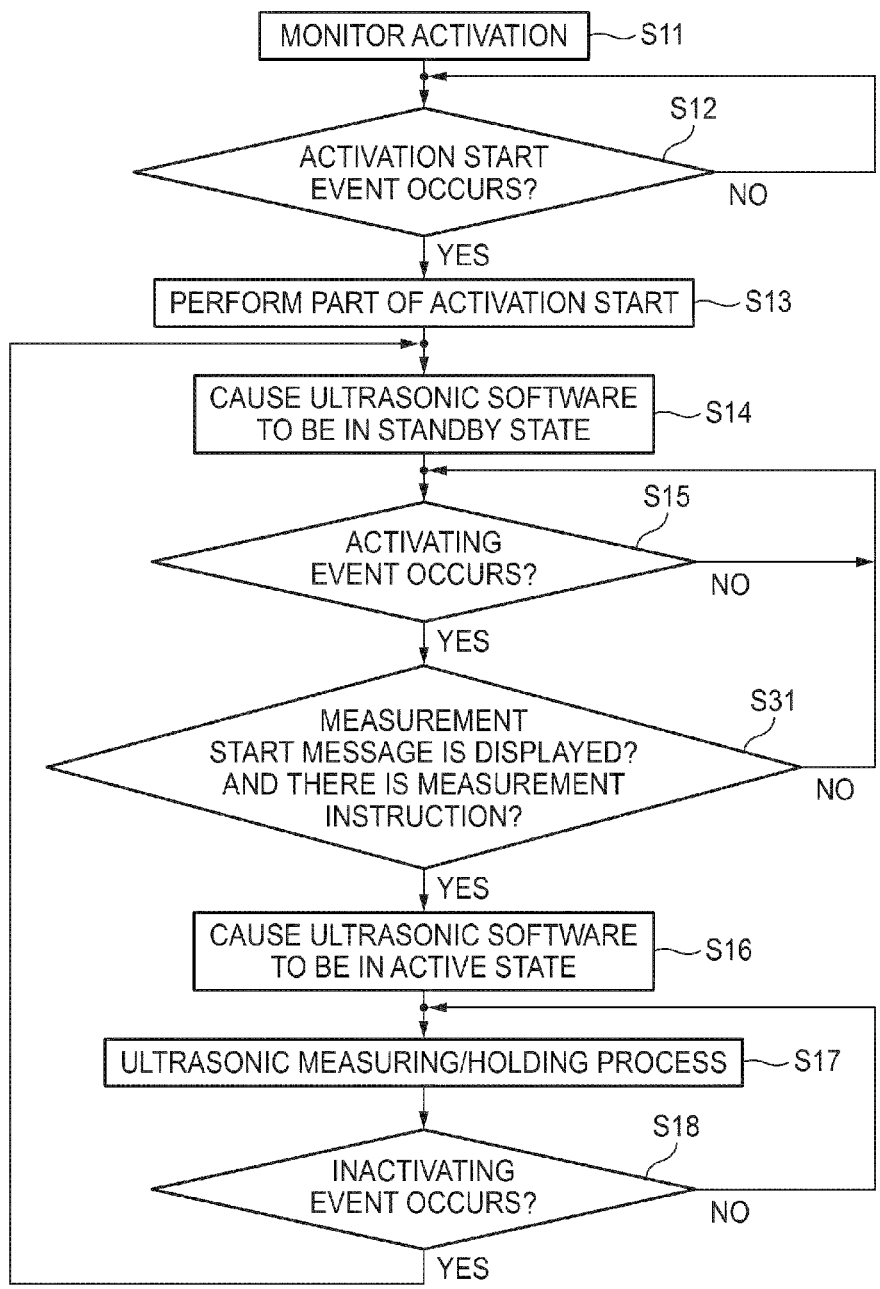
FIG. 6 is a flowchart illustrating an operation of an ultrasonic control section 18 according to a third embodiment.

Configurations of the vital sign measuring system 1 and the patient monitor 10 are similar to those of FIGS. 1 and 2. Operations of the ultrasonic control section 18 (the event detection part 181 and the software control part 182) according to the present embodiment will be described with reference to the flowchart of FIG. 6.

Similarly to the first embodiment, the ultrasonic control section 18 performs the processes until the activating event is detected (S11 to S15). It is assumed that the activating event is "at least one of the vital signs (a blood pressure, a body temperature, a breathing rate and the like) has the abnormal value". When the activating event has occurred, the software control part 182 displays a measurement start message of "Does start measurement of ultrasonic images?" on the display screen and displays buttons of "Yes" and "No" (S31). A user sets whether to start (activate) execution of the ultrasonic software by operating the buttons (S31).

When non-start (inactivation) of the measurement is selected (S31: No), the software control part 182 performs no processes and the event detection part 181 monitors the occurrence of the activating event again (S15). Even when the activating event has occurred again, the software control part 182 may control for preventing the measurement start message from being displayed for a predetermined time. Furthermore, the software control part 182 may allow the ultrasonic software to proceed to the ending state from the standby state.

When start (activation) of the measurement is selected (S31: Yes), the software control part 182 completes the activation process of the ultrasonic software and causes the ultrasonic software to be in the active state (S16).

In addition, the software control part 182 may change a button related to the ultrasonic software (color changing, flickering and the like) without displaying the measurement start message, or perform sound output together with the measurement start message. That is, the software control part 182 may perform output for promoting the activation of the ultrasonic software and complete the activation process when a user has selected the activation.

Subsequently, the effect of the patient monitor 10 according to the present embodiment will be described. As described above, when the activating event has occurred, the software control part 182 performs to output for promoting the activation of the ultrasonic software. When a user has selected the activation, the software control part 182 completes the activation of the ultrasonic software. A user can explicitly instruct the activation of the ultrasonic software, thereby operating the patient monitor 10 in an intended state. For example, in the case in which a user watches a change in the vital sign when the vital sign has the abnormal value, the patient monitor 10 can stably measure the vital sign without operating the ultrasonic software. On the other hand, when the user intends to understand a reason of the change in the vital sign from ultrasonic image, the patient monitor 10 can measure the vital sign and activate the ultrasonic software. In this way, it is possible to understand a reason of a change in a disease state of a subject from the ultrasonic images.

Fourth Embodiment

In the patient monitor 10 according to the present embodiment, the type of the activation start event and the activating event is switched according to a use scene (a use mode). The difference with the first embodiment will be described below.

Configurations of the vital sign measuring system 1 and the patient monitor 10 are similar to those of FIGS. 1 and 2. In the present embodiment, a user sets in advance the use mode with respect to the patient, monitor 10. Furthermore, a user may change setting of the use mode at an arbitrary timing during the use of the patient monitor 10. The use mode is for setting a place and a subject in/for which the patient monitor 10 is to be used. As an example of the use mode, there are an "ICU mode (a mode to be used in an ICU)", an "operating room mode (a mode to be used in an operating room)", a "ward mode (a mode to be used in a general ward)", an "abdominal disease mode (a mode to be used for a subject frequently requiring ultrasonic measurement", and the like.

A user defines these use modes and the activation start, event/the activating event in association with each other. FIG. 7 is a conceptual diagram illustrating an example of the association. In the present example, in the ICU mode, the activation start event is set, as "activation of the patient monitor 10" and the activating event is set as "probe detection (connection of the ultrasonic measuring device 20)". On the other hand, in the operating room mode, the activation start event is set as "probe detection (connection of the ultrasonic measuring device 20)" and the activating event is set as "change in received signals from the ultrasonic measuring device 20". The association may be held in the storage unit 17, for example.

The event detection part 181 detects the activation start event and the activating event based on the association. That is, the event detection part 181 reads the set use mode and the association (FIG. 7) from the storage unit 17, and specifies the activation start event and the activating event to be detected based on the use mode. For example, in the case in which the association of FIG. 7 is performed, when the use mode is the ICU mode, the event detection part 181 detects the "activation of the patient monitor 10" as the activation start event. On the other hand, when the use mode is the operating room mode, the event detection part 181 detects the "probe detection (connection of the ultrasonic measuring device 20)" as the activation start event.

In the association illustrated in FIG. 7, default values may be set in advance at the time of shipment of the patient monitor 10. Although not illustrated in FIG. 7, each use mode and the inactivating event may be associated with each other. A user may freely change setting of the content of the association (FIG. 7) while the patient monitor 10 is operating.

Subsequently, the effect of the patient monitor 10 according to the present embodiment will be described. The patient monitor 10 is used in all places in a hospital and used for a subject. Therefore, the importance of ultrasonic diagnosis differs according to the use mode. The event detection part 181 according to the present embodiment detects each event (the activation start event, the activating event, and the inactivating event) in consideration of the use mode. In this way, it is possible to quickly activate the ultrasonic software in a scene in which the importance of ultrasonic measurement is high. Furthermore, in a scene in which the importance of the ultrasonic measurement is low, since processes related to the ultrasonic software are not performed in the background, it is possible to smoothly perform other processes (acquirement and the like of the vital sign) and to reduce a load at the time of battery driving.

As described above, the invention made by the present inventor is described in detail based on the embodiments, but the present invention is not limited to the embodiments mentioned already and various modifications can be made without departing from the scope of the present invention.

In the above description, the patient monitor 10 acquires vital sign (the first vital sign information) and further acquires ultrasonic image (the second vital sign information); however, the patient monitor 10 is not always limited thereto. For example, the patient monitor 10 may be a device that acquires brain wave information or a device that acquires an electric impedance tomography signal, instead of a device that acquires an ultrasonic image from other devices. That is, the patient monitor 10 may acquire at least one of vital signs (the second vital sign information, for example, the ultrasonic image, the brain wave information, and the electric impedance tomography signal) from various devices connected to the patient monitor 10 in a wired manner or a wireless manner, in addition to the vital sign (the first vital sign information).

The above ultrasonic software is one aspect of the biological information processing software and uses the ultrasonic image as the second vital sign information, but the second vital sign information is not limited to the ultrasonic image. The vital sign information processing software may handle brain wave information or an electric impedance tomography signal as mentioned above. Also, the biological information processing software may display numerical information or waveform information of the second vital sign information. Further, the second vital signal information may be displayed with an aspect of image information similar to the ultrasonic image.

At least a part of the processes of the aforementioned control unit 14 (the ultrasonic control section 18) can be implemented as a computer program operating in the patient monitor 10.

The program can be stored using various types of non-transitory computer readable mediums, and can be supplied to a computer. The non-transitory computer readable medium includes various types of tangible storage mediums. An example of the non-transitory computer readable medium includes a magnetic recording medium (for example, a flexible disk, a magnetic tape, a hard disk drive), a magneto-optical recording medium (for example, a magneto-optical disk), a CD-ROM (Read Only Memory), a CD-R, a CD-R/W, a semiconductor memory (for example, a mask ROM, a PROM (Programmable ROM), an EEPROM (Erasable ROM), a flash ROM, a RAM (random access memory). Furthermore, the program may also be supplied to the computer by various types of transitory computer readable mediums. An example of the transitory computer readable medium includes an electrical signal, an optical signal, and an electromagnetic wave. The transitory computer readable medium can supply the program to the computer via a wired communication path such as an electric wire and an optical fiber or a wireless communication path.

The present application is based on Japanese Patent Application Nos. 2015-238119, filed on Dec. 7, 2015, and 2016-234159, filed on Dec. 1, 2016, the entire contents of which are incorporated herein by reference.

INDUSTRIAL APPLICABILITY

There is provided with a patient monitor with which, when the first vital sign information (vital sign) and the second vital sign information (for example, ultrasonic image) of a subject are acquired and displayed, it is possible to reduce a load of the activation process of the biological information processing software for the second vital sign information.

REFERENCE SIGNS LIST 1 vital sign measuring system
10 patient monitor
11 input interface
12 communication unit
13 operating unit
14 control unit
15 speaker
16 display unit
17 storage unit
18 ultrasonic control section
181 detection part
182 software control part
20 ultrasonic measuring device
21 prove
22 control unit
23 storage unit
30 sensor

The invention claimed is:

1. A patient monitor that acquires and displays first vital sign information and second vital sign information of a subject, the patient monitor comprising:
   a memory that stores biological information processing software pertaining to the second vital sign information, the second vital sign information includes an ultrasonic image of the subject; and
   a processor that executes the biological information processing software, wherein the processor is configured to control the patient monitor to:
      based on detecting a partial activation start event for starting an activation of the biological information processing software, perform a partial activation process of the biological information processing software, including at least one of reading a setting data, reading an ending state, ensuring of a work memory area, reading of a register and writing to the register, or establishing a connection with an ultrasonic measuring device, wherein during the partial activation process, the first vital sign information received from a sensor is displayed and the ultrasonic image of the subject based on received ultrasonic signals is not displayed;

based on the partial activation process having been completed, cause the biological information processing software to be in a standby state, wherein during the standby state, the first vital sign information received from the sensor is displayed and an ultrasonic image of the subject based on received ultrasonic signals is not displayed; and cause the biological information processing software to complete activation of the biological information processing software from the standby state and proceed to an active state based on detecting an activating event for activating the biological information processing software, wherein in the active state, the ultrasonic image of the subject based on the received ultrasonic signals is displayed on a display.

2. The patient monitor according to claim 1, wherein the processor is configured to control the patient monitor to:

detect an inactivating event which causes the biological information processing software to be in the standby state or an ending state, and when the inactivating event is detected, cause the biological information processing software to proceed to the standby state or the ending state from the active state.

3. The patient monitor according to claim 1, wherein the processor is configured to control the patient monitor to:

detect the activation start event based on an abnormal value of the first vital sign information of the subject having changed to a normal value.

4. The patient monitor according to claim 1, wherein the processor is configured to control the patient monitor to:

monitor the first vital sign information, and based on the first vital sign information of the subject having a normal value when the activating event is detected, allow the biological information processing software to proceed to the active state from the standby state.

5. The patient monitor according to claim 1, wherein the processor is configured to control the patient monitor to:

when the activating event is detected, perform an output of a request for activating the biological information processing software, and when an instruction for activating the biological information processing software is input, cause the biological information processing software to proceed to the active state from the standby state.

6. The patient monitor according to claim 1, wherein the processor is configured to control the patient monitor to:

specify the activation start event to be detected based on a use mode of the patient monitor.

7. The patient monitor according to claim 1, wherein the processor is configured to control the patient monitor to:

specify the activating event to be detected based on a use mode of the patient monitor.

8. The patient monitor according to claim 6, wherein setting of the use mode is arbitrarily changeable by a user.

9. A control method of a patient monitor that acquires and displays first vital sign information and second vital sign information of a subject, the control method comprising:

detecting an activation start event for starting an activation of biological information processing software pertaining to the second vital sign information, the second vital sign information includes an ultrasonic image of the subject;

based on the detecting the activation start event, performing a partial activation process of the biological information processing software, including at least one of reading a setting data, reading an ending state, ensuring of a work memory area, reading of a register and writing to the register, or establishing a connection with an ultrasonic measuring device, wherein during the partial activation process, the first vital sign information received from a sensor is displayed and the ultrasonic image of the subject based on received ultrasonic signals is not displayed;

based on the partial activation process having been completed, causing the biological information processing software to be in a standby state, wherein during the standby state, the first vital sign information received from the sensor is displayed and an ultrasonic image of the subject based on received ultrasonic signals is not displayed; and causing the biological information processing software to complete activation of the biological information processing software from the standby state and proceed to an active state based on detecting an activating event for activating the biological information processing software, wherein in the active state, the ultrasonic image of the subject based on the received ultrasonic signals is displayed on a display.

10. A non-transitory computer readable medium storing a program, which is used in a computer that acquires and displays first vital sign information and second vital sign information of a subject, and causes the computer to perform a method including:

detecting an activation start event for starting an activation of biological information processing software pertaining to the second vital sign information, the second vital sign information includes an ultrasonic image of the subject;

based on the detecting the activation start event, performing a partial activation process of the biological information processing software, including at least one of reading a setting data, reading an ending state, ensuring of a work memory area, reading of a register and writing to the register, or establishing a connection with an ultrasonic measuring device, wherein during the partial activation process, the first vital sign information received from a sensor is displayed and the ultrasonic image of the subject based on received ultrasonic signals is not displayed;

based on the partial activation process having been completed, causing the biological information processing software to be in a standby state, wherein during the standby state, the first vital sign information received from the sensor is displayed and an ultrasonic image of the subject based on received ultrasonic signals is not displayed; and causing the biological information processing software to complete activation of the biological information processing software from the standby state and proceed to an active state based on detecting an activating event for activating the biological information processing software, wherein in the active state, the ultrasonic image of the subject based on the received ultrasonic signals is displayed on a display.

* * * * *